(12) United States Patent
Frerichs

(10) Patent No.: US 6,929,728 B2
(45) Date of Patent: Aug. 16, 2005

(54) SENSOR FOR MEASURING A GAS CONCENTRATION OR ION CONCENTRATION

(75) Inventor: Heinz-Peter Frerichs, St. Peter (DE)

(73) Assignee: Micronas GmbH, Freiburg (DE)

( * ) Notice: Subject to any disclaimer, the term of this patent is extended or adjusted under 35 U.S.C. 154(b) by 310 days.

(21) Appl. No.: 10/121,935

(22) Filed: Apr. 12, 2002

(65) Prior Publication Data

US 2002/0157950 A1 Oct. 31, 2002

(30) Foreign Application Priority Data

Apr. 12, 2001 (DE) .......................... 101 18 367

(51) Int. Cl.⁷ ............................ G01N 27/414
(52) U.S. Cl. ............... 204/416; 204/431; 257/253; 422/82.03
(58) Field of Search ................ 204/416, 431; 422/82.03; 257/253

(56) References Cited

U.S. PATENT DOCUMENTS

| 4,385,274 A | 5/1983 | Shimada et al. ........... 324/71.6 |
| 4,411,741 A | 10/1983 | Janata |
| 5,071,770 A | * 12/1991 | Kolesar, Jr. ................ 436/151 |
| 5,911,873 A | 6/1999 | McCarron et al. |
| 5,944,970 A | * 8/1999 | Rosenblatt ................. 204/416 |

FOREIGN PATENT DOCUMENTS

| DE | 3144459 | 10/1982 |
| DE | 4239319 | 4/1993 |
| DE | 4333875 | 4/1995 |
| DE | 19849932 | 5/2000 |
| EP | 0947829 | 10/1999 |

OTHER PUBLICATIONS

Gergintschew et al., "The capacitively controlled field effect transistor (CCFED) as a new low power gas sensor", Elsevier Science S.A., B 35–36, 1996, 285–289.

* cited by examiner

Primary Examiner—Kaj K. Olsen
(74) Attorney, Agent, or Firm—O'Shea, Getz & Kosakowski, P.C.

(57) ABSTRACT

The invention relates to a sensor for measuring a gas concentration or ion concentration which has a substrate (11), a drain (3) formed on the substrate, a source (2) formed on the substrate, a channel area (4) of the substrate located between drain (3) and source (2), a conductive guard ring (1) located outside the channel area, and a sensitive gate layer (8) whose potential depends on the surrounding gas or ion concentration, with an air gap (10) provided between the gate layer and channel area (4). In order to create a sensor that can be made economically and compactly which nevertheless ensures exact measurement of a change in concentration with time, it is provided that surface profiling (7 and 12) be formed between guard ring (1) and channel area (4).

10 Claims, 1 Drawing Sheet

SENSOR FOR MEASURING A GAS CONCENTRATION OR ION CONCENTRATION

BACKGROUND OF THE INVENTION

The present invention relates to the field of sensors for measuring a gas concentration or ion concentration.

Sensors with field effect transistors (FETs) that have an ion-sensitive layer used as a gate are used to measure ion concentrations, with the potential of the layer depending on the ion concentration of a surrounding fluid or gas. For example, U.S. Pat. No. 5,911,873 shows such an ion-sensitive FET (ISFET). In addition, sensors with FETs are known for measuring gas concentrations, for example from U.S. Pat. No. 4,411,741, which have a gas-sensitive layer used as a gate, whose work function depends on the surrounding gas concentration.

Such sensors are generally produced from a drain and a source in a semiconductor substrate by counterdoping, and an insulating layer is grown or deposited on the substrate between the source and the drain. An ion-sensitive layer can be applied directly to this insulating layer. A gas-sensitive layer called a suspended gate FET (SGFET) can be applied at a certain distance. Alternatively, a gate can be applied to the insulator that is controlled capacitively by a gas-sensitive gate applied at a certain distance. This type of sensor is referred to as a capacitive-controlled FET (CCFET), and is described for example in German patent document DE 43 33 875 C2.

One disadvantage of this arrangement is that because of the ever-present surface conductivity, the potential is drawn over the FET after a certain period of time to the potential that is applied to the gas-sensitive gate, which causes a drift of the drain source current. To prevent this, a conductive ring, also called a guard ring and connected to a definite potential is applied conventionally to the FET. With such an arrangement, the channel area of the FET, because of the surface conductivity of the area between the guard ring and the channel area, assumes the potential of the guard ring after a certain period of time. The distance of the guard ring from the channel area of the FET and the conductivity of the surface define the time until the channel area assumes the guard ring potential, so that the minimum possible concentration change per unit time that a gas signal to be detected must have in order to be recorded is established. This distance determines the size, and as a result also the manufacturing cost of such a sensor.

Therefore, there is a need for a sensor for measuring an ion concentration or a gas concentration, which is economical, compact, and ensures measurement accuracy for the change in concentration with time.

SUMMARY OF THE INVENTION

Briefly, according to an aspect of the invention, the distance between the guard ring and the FET is increased without a circuit of larger dimensions being required. The current path can be extended by surface profiling, and therefore the RC time that defines the adjustment of the FET potential to the potential of the guard ring is increased without the functional ability of the sensor arrangement being adversely affected by surface profiling.

Surface profiling can be performed by forming spaced elevations at a distance from one another on a previously produced thick oxide layer. Even larger elevations can be formed in the air gap between the sensitive gate layer and the thin oxide layer via the channel area.

These and other objects, features and advantages of the present invention will become more apparent in light of the following detailed description of preferred embodiments thereof, as illustrated in the accompanying drawings.

DETAILED DESCRIPTION OF THE INVENTION

A gas sensor has a first charge carrier type on a substrate 11 (e.g., n-doped silicon), a source 2, and a drain 3 of a second type of charge carrier, for example made of p-doped silicon, formed for example by ion implantation.

Figure 1:
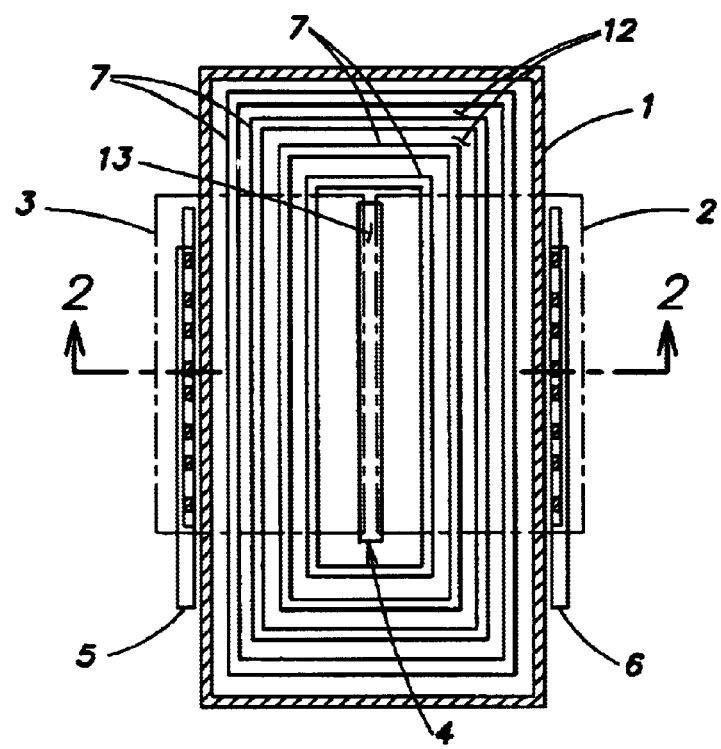
FIG. 1 is a top view of a sensor according to one embodiment of the invention.
Figure 2:
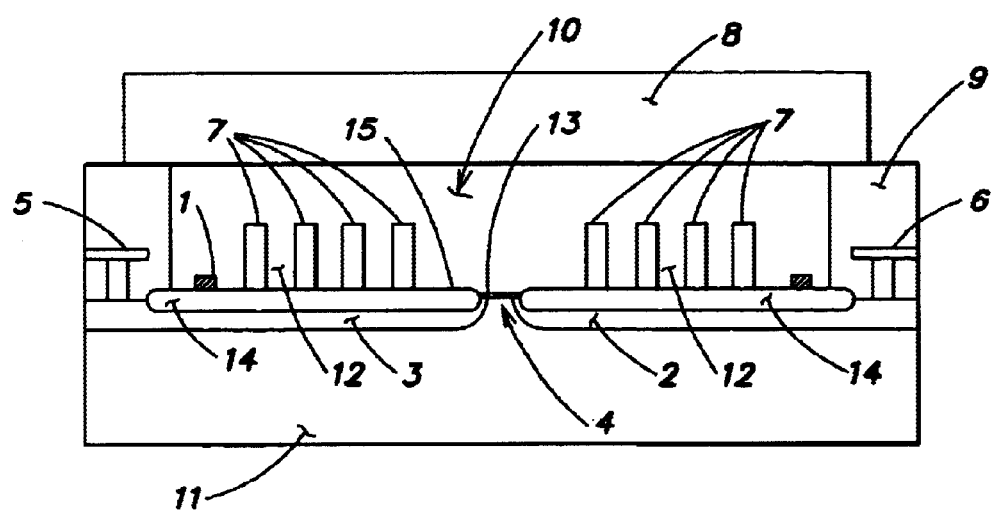
FIG. 2 is a section along line 2—2 in FIG. 1.

The source 2 is provided with a source lead 6, and the drain 3 is provided with a drain lead 5. A channel area 4 is provided in the substrate between the source 2 and the drain 3 on which a thin oxide layer 13 is formed. Insulating layers, for example thick oxide layers 14, are formed on the source 2 and the drain 3 to the surface 15 of which layers a guard ring 1 made of a conductive material is applied. As shown in FIG. 1, the guard ring 1 runs around the channel area 4 and can be set at a specific potential.

A gas-sensitive gate layer 8 is located on lateral insulating areas 9, whose potential depends on the surrounding gas concentration. An air gap 10 is formed between the gate layer 8 and the thin oxide layer 13. The thin oxide layer 13 works with the air gap as a gate dielectric. Changes in the gas concentration can thus be detected as changes in the source-drain current.

According to an aspect of the invention, surface profiling is provided between the thin oxide layer 13 above the channel area 4 and the guard ring 1, which has elevations 7 with depressions 12 formed between them. The profiling of the surface 15 can be formed in particular by applying layers on the thick oxide layer 14 by appropriate deposition steps, after which the depressions are revealed in etching steps defined by photo masks.

The thin oxide layer 13 can be made as a capacitor, as disclosed in co-pending application filed even date herewith and designated Ser. No. 10/121,920, entitled "SENSOR FOR MEASURING AN ION CONCENTRATION OR GAS CONCENTRATION".

Although the present invention has been shown and described with respect to several preferred embodiments thereof, various changes, omissions and additions to the form and detail thereof, may be made therein, without departing from the spirit and scope of the invention.

What is claimed is:

1. A sensor for measuring a gas concentration or ion concentration, said sensor comprising: a substrate of a first charge carrier type, a drain of a second charge carrier type formed on the substrate, a source of the second charge carrier type formed on the substrate, a channel area of the substrate located between the drain and the source, a conductive guard ring located outside the channel area, and a sensitive gate layer whose potential depends on the surrounding gas or ion concentration, with an air gap being provided between the gate layer and the channel area, wherein surface profiling is formed between the guard ring and the channel area, the surface profiling having elevations and depressions, the elevations being applied to a surface between an insulating thin layer in the channel area and the guard ring by deposition with the depressions formed between the elevations, the elevations being applied as insulating material to one or more insulating layers, and wherein the elevations are formed substantially concentrically with respect to the channel area.

2. The sensor as claimed in claim 1, wherein the elevations are uniformly spaced.

3. The sensor as claimed in claim 1, wherein the sensitive gate layer is a gas-sensitive gate layer.

4. The sensor as claimed in claim 1, wherein the one or more insulating layers include at least one thick oxide layer.

5. A sensor for measuring a gas concentration or ion concentration, said sensor comprising:

a substrate of a first charge carrier type;

a drain of a second charge carrier type formed on the substrate;

a source of the second charge carrier type formed on the substrate;

a channel area of the substrate located between the drain and the source;

a conductive guard ring located outside the channel area;

a sensitive gate layer whose potential depends on the surrounding gas or ion concentration;

an air gap provided between the gate layer and the channel area; and a contoured surface including at least one elevation and at least one depression, the contoured surface being formed between the guard ring and the channel area, wherein the at least one elevation is formed substantially concentrically with respect to the channel area.

6. The sensor as claimed in claim 5, wherein the contoured surface includes a plurality of alternating elevations and depressions.

7. The sensor as claimed in claim 5, wherein the at least one elevation is applied to a surface between an insulating thin layer in the channel area and the guard ring by deposition with the depressions being formed there between.

8. The sensor as claimed in claim 5, wherein the at least one elevation is applied as insulating material to one or more insulating layers.

9. The sensor as claimed in claim 5, wherein the sensor includes a plurality of elevations that are uniformly spaced.

10. A sensor for measuring a gas concentration or ion concentration, said sensor comprising:

a substrate of a first charge carrier type;

a drain of a second charge carrier type formed on the substrate;

a source of the second charge carrier type formed on the substrate;

a channel area of the substrate located between the drain and the source;

a conductive guard ring located outside the channel area;

a sensitive gate layer whose potential depends on the surrounding gas or ion concentration;

an air gap provided between the gate layer and the channel area; and a contoured surface including a plurality of elevations and a plurality of depressions that are formed between the guard ring and the channel area, wherein the plurality of elevations are substantially concentric with respect to the channel area.

* * * * *